Figure 1:
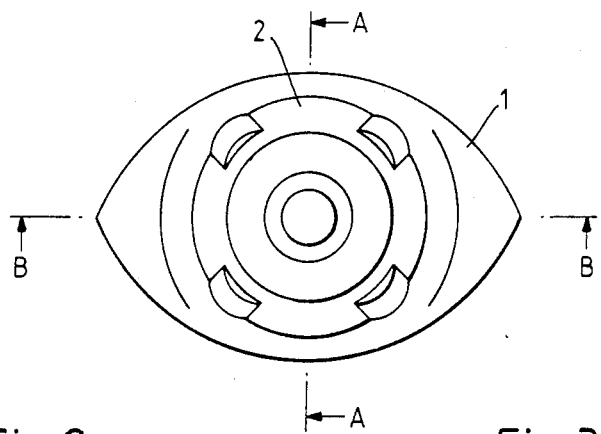

United States Patent [19]

Pirilä

[11] Patent Number: 4,936,498
[45] Date of Patent: Jun. 26, 1990

[54] TIP PART OF A DOSAGE VESSEL

[75] Inventor: Veikko Pirilä, Hyrylä, Finland

[73] Assignee: Oy Star Ab, Finland

[21] Appl. No.: 254,476

[22] PCT Filed: Mar. 21, 1988

[86] PCT No.: PCT/FI88/00040
§ 371 Date: Sep. 22, 1988
§ 102(e) Date: Sep. 22, 1988

[87] PCT Pub. No.: WO88/07359
PCT Pub. Date: Oct. 6, 1988

[30] Foreign Application Priority Data

Mar. 24, 1987 [FI] Finland .................................. 871292

[51] Int. Cl.$^5$ ............................................. B65D 47/18
[52] U.S. Cl. .................................... 222/420; 222/215; 222/564
[58] Field of Search ............... 222/206, 212, 215, 420, 222/421, 422, 547, 564, 571; 604/294–302

[56] References Cited

U.S. PATENT DOCUMENTS

| 878,668 | 2/1908 | Phelps et al. | |
| 1,970,688 | 8/1934 | Callahan | 222/420 |
| 2,832,513 | 4/1958 | Tubin | |
| 2,874,881 | 2/1959 | Stull | 222/421 |
| 2,925,200 | 2/1960 | Cabe | 222/215 X |
| 2,987,223 | 6/1961 | Armour | 222/566 X |

FOREIGN PATENT DOCUMENTS

| 213556 | 12/1956 | Australia | 222/215 |
| 365708 | 8/1919 | Fed. Rep. of Germany | 222/421 |
| 2581975 | 11/1986 | France | 222/421 |

Primary Examiner—Kevin P. Shaver
Attorney, Agent, or Firm—Burns, Doane, Swecker & Mathis

[57] ABSTRACT

Tip part (3) of a dosage vessel (1) for the dosage of liquid dropwise through a downwardly directed tip part. The tip part is provided with a capillary exhaust duct (6) as well as with a neck duct (8) wider than the exhaust duct. The liquid having access through the neck duct out of the vessel (1) into the exhaust duct (6). The neck duct (8) contains an oblong member (5) parallel to the neck duct.

19 Claims, 2 Drawing Sheets

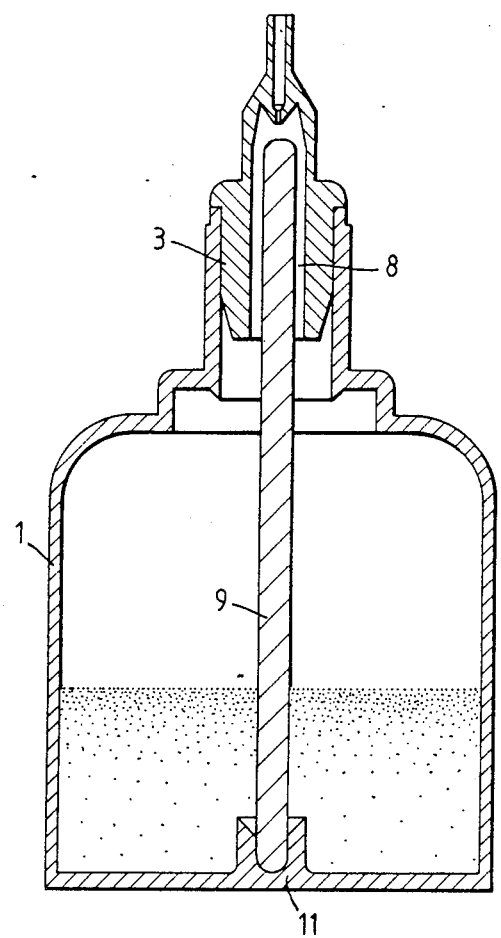

TIP PART OF A DOSAGE VESSEL

The present invention concerns the tip part of a dosage vessel for the dosage of liquid dropwise through a downwardly directed tip part, which is provided with a capillary exhaust duct as well as with a neck duct wider than the exhaust duct, the liquid having access through said neck duct out of the vessel into the exhaust duct.

For the dosage of various solutions dropwise, plastic bottles made of flexible plastic, e.g. polyethylene, are commonly used, out of which liquid is applied dropwise through a small opening provided in the mouth of the bottle by pressing the sides of the bottle which has been turned upside down.

In particular in the application of eye drops, it would be important to be able to apply the drops as of a size as uniform as possible while avoiding excessively large drops. In prior-art dropping bottles, one of the problems has been that the drop may fall off the bottle even before the bottle has been pressed, or that several drops fall at a time.

It is known in prior art that the dropping of several drops at a time can be prevented by using a choke in the narrow exhaust duct passing to the exhaust opening. A tip part in which an exhaust duct provided with a narrower portion is used is described, e.g., in the U.S. Pat. No. 2,987,223. The narrower portion is located at the inner end of the exhaust duct.

It is also known that the outer diameter of the exhaust duct projecting outwards from the tip part affects the size of the drop that is formed. With the prior-art dropping bottles and with water solutions, it has been noticed that the drop size is about 35 ... 50 µl, as a rule about 40 ... 50 µl, when various eye drops are applied. It is also possible to reduce the drop size by adding to the liquid, some additive that lowers the surface tension. A smaller drop size would be preferable, because on blinking of the eye, a major part of the drop applied to the eye is washed off the eye and ends up in the nasolacrimal duct and in the throat. Several eye drops may have detrimental side effects by this way. Of course, a smaller drop size would also be preferable out of the reason that the same bottle would be sufficient for a longer time of use. Moreover, a smaller drop size also permits a more accurately graded dosage when the dosage consists of several small drops.

When a bottle, e.g., in accordance with the U.S. Pat. No. 2,987,223 is used, the accuracy of dosage is deteriorated, among other things, by the fact that liquid often remains in the tip part, which liquid alters the drop size when drops are applied next time, e.g., by forming bubbles and splashes with air. This problem is harmful in particular when the drop size is reduced.

For allergy testing on the skin, smaller drops of uniform size are also needed, e.g. when various test patches are used.

The object of the present invention is to reduce the drop size with dropping bottles as well as to improve the accuracy of dosage. The tip part of a dosage vessel in accordance with the invention is characterized in that the neck duct contains an oblong member parallel to the neck duct.

During application of drops, the liquid moves outwards through the capillary exhaust duct, and no replacement air passes in. After the bottle has been, upon dosage, turned back to the standing position with its tip upwards, replacement air flows through the same duct from outside into the vessel.

In numerous tests it has been noticed that in a tip part in accordance with the invention the above oblong member in the neck duct guides the liquid and any air that may be contained in the liquid in the desired way back into the bottle after the application of drops, after the bottle has been turned to the standing position, whereby no liquid or foam consisting of liquid and air remains in the tip part. Thereby the reproductions of the droppings are optimal. When a tip part in accordance with the invention is used, the drop size can be reduced down to about 15 µl, and even below that.

Figure 2:
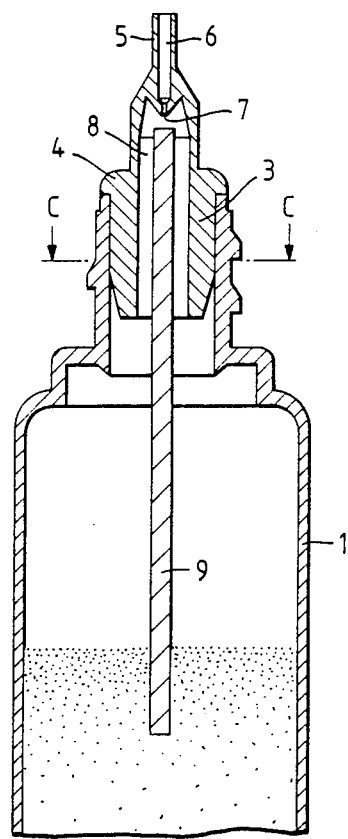
Figure 3:
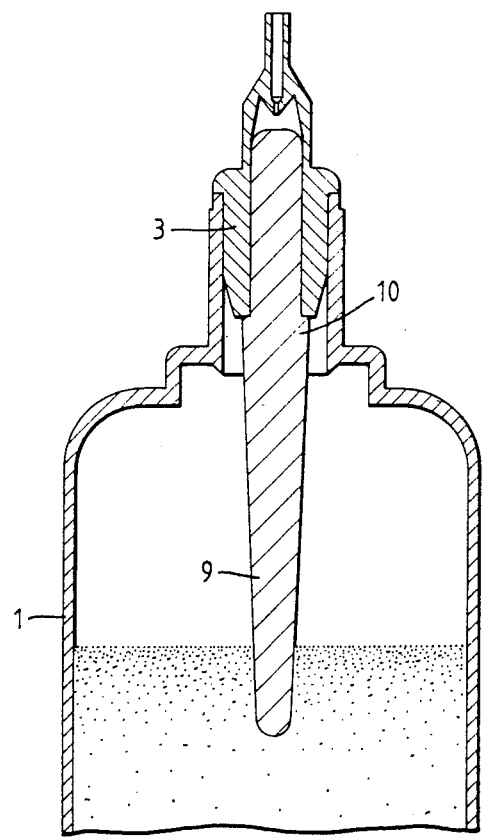

The invention and its details will be described in more detail in the following with reference to the accompanying drawings, wherein the dosage bottle and the tip part in accordance with the invention are shown on an about 3 times enlarged scale and wherein FIG. 1 is a top view of a dosage bottle sealed by a screw cap, FIG. 2 shows a section A—A in FIG. 1, without a screw cap, FIG. 3 shows a section B—B in FIG. 1, without a screw cap, FIG. 4 shows a section C—C in FIG. 2, without a dosage bottle, and FIG. 5 is a sectional view of an alternative embodiment.

The dosage bottle 1 is made of flexible plastic. The bottle is provided with a screw cap 2, by means of which it can be sealed when it is not used.

Into the neck portion of the bottle 1, a tip part 3 is inserted, which is placed tightly against the inner face of the neck portion of the bottle. A shoulder 4 on the circumference of the tip part prevents pressing of the tip part excessively deep into the bottle. The tip part terminates at the top in a narrow exhaust tube 5.

The inner capillary exhaust duct 6 in the exhaust tube 5 is, at its bottom end, provided with a narrower choke portion 7. The outer diameter of the exhaust tube is, e.g., 1.2 mm, and the inner diameter of the exhaust duct, e.g., 0.7 to 0.9 mm. Below the exhaust duct 6, the tip part is provided with a concentric neck duct 8, which is wider than the exhaust duct and whose inner diameter is, e.g., 3 to 4 mm. At the junction of the exhaust duct 6 and the neck duct 8, the inner wall of the tip part is chamfered downwards towards the axis of the ducts so that the inner face forms, e.g., a downwardly narrowing conical face. The junction point may also be shaped in a different way.

In the neck duct 8, a flat oblong additional piece 9 parallel to the neck duct is fitted. In the embodiment shown in FIGS. 2 to 4, the width of the top end of the additional piece equals the inner diameter of the neck duct, and the fitting is to such an extent tight that it remains in its position after it has been inserted into the neck duct. The shoulders 10 of the additional piece, which become placed against the lower edge of the tip part, cause the additional piece to be positioned at the correct depth. The correct depth may, of course, also be controlled in some other way, without shoulders. The top end of the additional piece 9 extends to immediate proximity of the lower end of the exhaust duct 6. The distance of the additional piece from the lower end of the exhaust duct is such that, when disturbing the surface tension forces, it breaks the liquid column or drop formed in the neck duct. In this way, the liquid can escape from the neck duct and, on its way, pulls the capillary empty. The suitable distance depends on the diameter of the neck duct and on the properties of the liquid, above all on the surface tension. When the diameter of the neck duct is 3 mm and when ordinary water solutions are used, a favourable distance is at the maximum about 2 mm, preferably less than 1 mm.

The lower end of the additional piece extends from the lower end of the tip part through the neck portion of the bottle into the container part of the bottle.

FIG. 5 shows an alternative embodiment. In it a cylindrical additional piece 9 is attached to the bottom of the bottle 1, whereat it does not have to be attached to the neck duct 8 in the tip part.

When liquid contained in the bottle is supposed to be administered dropwise, the screw cap of the bottle is removed and the tip part is turned facing downwards. When the sides of the bottle are pressed inwards, a drop can be made to fall out of the exhaust duct. Thereupon, when the bottle is turned back to the standing position, the additional piece extending to the proximity of the lower end of the exhaust duct causes the tip part to be emptied and the liquid remaining therein to flow back into the bottle.

In the drawings, the bottle is illustrated as standing, with the exhaust duct directed upwards. The expressions "upper" and "lower" used above in relation to the drawings consequently relate to the position shown in the drawings, which is changed when the bottle is turned to the dropping position.

The invention is not confined to the dosage of eye drops alone, but it may be applied equally well to accurate dropwise application of any liquid whatsoever, for example various test reagents.

The dimensioning of the different parts of the tip part depends, e.g., on the surface tension and viscosity of the liquid to be dropped and on the desired drop size. The suitable distance of the additional piece from the exhaust duct also depends on the diameter of the neck duct.

The additional piece may also be substituted for by a part made of one piece with the tip part. The additional piece may also be shorter, and its lower end may end at the level of the lower end of the neck duct or at its proximity. The joint between the neck-duct wall and the additional piece need not extend over the entire length of the neck duct, but only over a part of it. The cross section of the additional piece may also vary.

What is claimed is:

1. A tip part of a flexible dosage vessel for providing a dosage of liquid dropwise through the tip when downwardly turned comprising:
    a capillary exhaust duct,
    a neck duct, larger in diameter than the exhaust duct, the liquid having access through said neck duct out of the vessel and into the exhaust duct,
    an oblong member contained in and parallel to said neck duct and dividing said neck duct into at least two fluid passages which are parallel to and run in the direction of the oblong member,
    an exhaust tube, which extends from the neck duct, and contains said exhaust duct;
    whereby liquid can be dosed by compressing the dosage vessel in an inverted position, and after dosing some liquid the vessel can be turned back over so that the tip part is above the dosage vessel.

2. A tip part as claimed in claim 1, wherein the oblong member extends in the neck duct to cause the liquid to flow out of the neck duct back into the dosage vessel.

3. A tip part as claimed in claim 1, wherein the oblong member extends in the neck duct to affect the surface tension forces of the liquid present in the neck duct over the entire length of the neck duct.

4. A tip part as claimed in any of the claim 1, wherein the oblong member in the neck duct is located along a central axis of the exhaust duct.

5. A tip part as claimed in claim 1, wherein the oblong member in the neck duct is attached to the wall of the neck duct.

6. A tip part as claimed in claim 1, wherein the oblong member in the neck duct is attached to the bottom of the dosage vessel.

7. A tip part as claimed in claim 1, additionally comprising a lower end of the oblong member in the neck duct extending to an immediate proximity of the lower end of the neck duct.

8. A tip part as claimed in claim 7, wherein the oblong member in the neck duct extends in the neck duct to cause the liquid to flow out of the neck duct back into the dosage vessel.

9. A tip part as claimed in claim 1, wherein the oblong member in the neck duct extends to below the neck duct.

10. A tip part as claimed in claim 9, wherein the oblong member in the neck duct extends in the neck duct to cause the liquid to flow out of the neck duct back into the dosage vessel.

11. A tip part as claimed in claim 1, additionally comprising an upper end of the oblong member in the neck duct extending through the neck duct to an immediate proximity of the exhaust duct.

12. A tip part as claimed in claim 11, wherein the oblong member in the neck duct extends in the neck duct to cause the liquid to flow out of the neck duct back into the dosage vessel.

13. A tip part as claimed in claim 11, wherein the oblong member in the neck duct extends in the neck duct to affect the surface tension forces of the liquid present in the neck duct over the entire length of the neck duct.

14. A tip part as claimed in claim 11, wherein the oblong member in the neck duct extends to below the neck duct.

15. A tip part as claimed in claim 14, wherein the oblong member in the neck duct extends in the neck duct to cause the liquid to flow out of the neck duct back into the dosage vessel.

16. A tip part as claimed in claim 11, wherein a lower end of the oblong member in the neck duct extends to an immediate proximity of a lower end of the neck duct.

17. A tip part as claimed in claim 16, wherein the oblong member in the neck duct extends in the neck duct to cause the liquid to flow out of the neck duct back into the dosage vessel.

18. A tip part as claimed in claim 16, wherein the oblong member in the neck duct extends to below the neck duct.

19. A tip part as claimed in claim 18, characterized in that the oblong member in the neck duct extends in the neck duct to cause the liquid to flow out of the neck duct back into the dosage vessel.

* * * * *